(12) United States Patent
Baragona et al.

(10) Patent No.: US 10,130,452 B2
(45) Date of Patent: Nov. 20, 2018

(54) ORAL CLEANING DEVICE WITH ADJUSTABLE FLUID DYNAMICS

(71) Applicant: KONINKLIJKE PHILIPS N.V., Eindhoven (NL)

(72) Inventors: Marco Baragona, Delft (NL); Yu-Wen Chang, Mercer Island, WA (US); Milica Kovacevic Milivojevic, Eindhoven (NL); Valentina Lavezzo, Heeze (NL); Bart Gottenbos, Budel (NL); Sandra Hotzl, Eindhoven (NL); Quintin Oliver Williams, Eindhoven (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 0 days.

(21) Appl. No.: 14/900,203

(22) PCT Filed: May 5, 2015

(86) PCT No.: PCT/IB2015/053270
§ 371 (c)(1),
(2) Date: Dec. 21, 2015

(87) PCT Pub. No.: WO2015/173691
PCT Pub. Date: Nov. 19, 2015

(65) Prior Publication Data
US 2017/0056142 A1    Mar. 2, 2017

Related U.S. Application Data

(60) Provisional application No. 61/994,466, filed on May 16, 2014.

(51) Int. Cl.
*A61C 17/00* (2006.01)
*A61C 17/02* (2006.01)
(Continued)

(52) U.S. Cl.
CPC .......... *A61C 17/028* (2013.01); *A61C 1/0015* (2013.01); *A61C 1/0092* (2013.01);
(Continued)

(58) Field of Classification Search
CPC .. A61H 13/005; A61C 1/0007; A61C 1/0015; A61C 1/0092; A61C 17/00; A61C 17/02;
(Continued)

(56) References Cited

U.S. PATENT DOCUMENTS 3,590,813 A    7/1971  Roszyk
5,344,317 A *  9/1994  Pacher ............... A61C 17/02
                                                       433/100
(Continued)

FOREIGN PATENT DOCUMENTS

CN     101076298 A    11/2007
CN     102008359 A    4/2011
(Continued)

OTHER PUBLICATIONS

CENSE: "A Spray Based Method for Biofilm Removal"; Technische Universiteit Eindhoven, 005, PhD Thesis,180 Page Document.

*Primary Examiner* — Michael Tsai
*Assistant Examiner* — Christopher Miller

(57) ABSTRACT

An oral cleaning device (100) including: a nozzle portion (30) configured to direct a plurality of liquid droplets; an actuator (120); a mode selector (130); a liquid reservoir (38) wherein in operation liquid is moved from the liquid reservoir into an orifice (36) at the proximal end of the nozzle; a system (12, 13, 14, 24) configured to drive a plunger or piston element (16) toward the proximal end of the nozzle to create a spray of liquid droplets when the moving air comes into contact with the liquid; a control unit (15) configured to control the system to drive the plunger a predetermined number of times in response to a single actuation of the
(Continued)

actuator, where the control unit is further configured to accept input from the user via the mode selector, and the mode selector is configured for the user to select a number of liquid bursts that will be delivered in response to a single actuation of the actuator.

10 Claims, 7 Drawing Sheets

(51) Int. Cl.
    *A61C 17/028*     (2006.01)
    *A61H 13/00*     (2006.01)
    *A61C 1/00*     (2006.01)

(52) U.S. Cl.
    CPC ....... *A61C 17/0202* (2013.01); *A61H 13/005* (2013.01); *A61C 1/0007* (2013.01); *A61H 2201/5043* (2013.01)

(58) Field of Classification Search
    CPC .. A61C 17/0202; A61C 17/028; A61C 1/0061
    USPC .................... 433/80, 84, 85, 88–90, 98–100; 601/159–165
    See application file for complete search history.

(56) References Cited

U.S. PATENT DOCUMENTS

| | | | | |
|---|---|---|---|---|
| 5,370,630 A * | 12/1994 | Smidebush | A61M 5/2053 | 604/209 |
| 5,882,319 A * | 3/1999 | Olson | A61H 9/00 | 601/155 |
| 6,482,356 B1 * | 11/2002 | Brown | A61C 1/00 | 134/100.1 |
| 2001/0012605 A1 | 8/2001 | Kawamura | | |
| 2002/0082545 A1 * | 6/2002 | Sennett | A61C 17/0202 | 604/32 |
| 2004/0209222 A1 * | 10/2004 | Snyder | A61C 17/02 | 433/80 |
| 2005/0271531 A1 * | 12/2005 | Brown, Jr. | A61C 1/0061 | 417/474 |
| 2005/0272001 A1 * | 12/2005 | Blain | A61C 1/0061 | 433/80 |
| 2005/0272002 A1 | 12/2005 | Chenvainu et al. | | |
| 2007/0141529 A1 * | 6/2007 | Bouneff | A61C 1/0007 | 433/118 |
| 2007/0154863 A1 * | 7/2007 | Cai | A46B 11/0058 | 433/89 |
| 2007/0157404 A1 | 7/2007 | Brewer et al. | | |
| 2007/0203439 A1 * | 8/2007 | Boyd | A61C 1/0084 | 601/162 |
| 2007/0221681 A1 * | 9/2007 | Eisinga | A45D 34/04 | 222/23 |
| 2007/0248932 A1 | 10/2007 | Gharib et al. | | |
| 2007/0254260 A1 * | 11/2007 | Alden | A46B 15/0055 | 433/85 |
| 2007/0299396 A1 | 12/2007 | Rocklin | | |
| 2008/0014548 A1 * | 1/2008 | Paxton | A61C 17/0202 | 433/90 |
| 2008/0313829 A1 * | 12/2008 | Dabrowski | A61C 17/221 | 15/22.1 |
| 2009/0017423 A1 * | 1/2009 | Gottenbos | A61C 17/028 | 433/216 |
| 2009/0060622 A1 * | 3/2009 | Lian | A46B 11/0006 | 401/28 |
| 2009/0143914 A1 * | 6/2009 | Cook | A46B 15/0002 | 700/275 |
| 2009/0305187 A1 * | 12/2009 | Janssen | A61C 17/0202 | 433/88 |
| 2010/0151414 A1 * | 6/2010 | Paxton | A61C 17/0202 | 433/90 |
| 2010/0167236 A1 | 7/2010 | Edwards et al. | | |
| 2010/0284728 A1 * | 11/2010 | Heil | A61C 17/227 | 401/270 |
| 2010/0304327 A1 | 12/2010 | Grez et al. | | |
| 2011/0207078 A1 * | 8/2011 | Johnson | A61C 17/028 | 433/88 |
| 2011/0282248 A1 * | 11/2011 | Martin | A61J 7/0061 | 601/1 |
| 2012/0183926 A1 * | 7/2012 | Shalev | A61C 17/028 | 433/215 |
| 2012/0270178 A1 * | 10/2012 | Black | A61C 17/0202 | 433/89 |
| 2014/0154640 A1 * | 6/2014 | Mok | A61C 1/0092 | 433/89 |
| 2014/0259474 A1 * | 9/2014 | Sokol | A61C 17/3445 | 15/22.2 |
| 2014/0272782 A1 * | 9/2014 | Luettgen | A61H 13/005 | 433/80 |
| 2014/0363784 A1 * | 12/2014 | Monty | A61C 1/0046 | 433/29 |
| 2014/0371643 A1 * | 12/2014 | Martin | A61C 5/90 | 601/159 |

FOREIGN PATENT DOCUMENTS

| | | |
|---|---|---|
| DE | 19601244 A1 | 7/1997 |
| JP | 2000157562 A | 6/2000 |
| WO | 2013061251 A1 | 5/2013 |
| WO | 2013093717 A1 | 6/2013 |
| WO | 2013098691 A1 | 7/2013 |
| WO | 2013190428 A1 | 12/2013 |

\* cited by examiner

ORAL CLEANING DEVICE WITH ADJUSTABLE FLUID DYNAMICS

CROSS-REFERENCE TO PRIOR APPLICATIONS

This application is the U.S. National Phase application under 35 U.S.C. § 371 of International Application No. PCT/IB2015/053270, filed on May 5, 2015, which claims the benefit of U.S. Provisional Patent Application No. 61/994,466, filed on May 16, 2014. These applications are hereby incorporated by reference herein.

FIELD OF THE INVENTION

The present disclosure is directed generally to oral care appliances for cleaning teeth with a user-adjustable sequence of coordinated bursts of air and fluid.

BACKGROUND

Oral care appliances that clean the teeth with streams or bursts of liquid or a mixture of liquid droplets and air are effective at disrupting biofilm in the oral cavity, particularly in the interproximal areas of the teeth. These appliances generally create liquid droplets when the liquid is brought into contact with a high velocity stream of air using a pump or similar arrangement.

Coordinated bursts of liquid and air use far less liquid per cleaning compared to a continuous stream of liquid. As a result, less liquid is used per cleaning and the user does not accumulate an uncomfortable volume of liquid in the mouth. This is particularly beneficial when the liquid is a mouthwash or similar liquid which shouldn't be swallowed by the user. Additionally, the alternating bursts of air and liquid provide superior biofilm removal and interdental cleaning.

However, existing oral care devices using coordinated bursts of liquid and air typically have a single setting of either ON or OFF. When the device is OFF, no bursts are produced. When the device is ON, the device produces a non-variable predetermined or preprogrammed pattern of coordinated liquid and air bursts. Accordingly, the user is not able to adjust the bursts to account for variations in oral cleanliness, sensitivity, liquid use, or other factors. There may be scenarios where, for example, the user would like to use more bursts than might normally be provided, in order to provide an intense cleaning session. In other scenarios, the user may want to conserve liquid and provide a light cleaning session.

In devices where the bursts are variable but are individually triggered by manual activation or firing, the repetitive motion by the user quickly becomes monotonous and can be a physical strain.

Accordingly, there is a need in the art for oral cleaning devices that provide user-adjustable coordinated bursts of liquid and air.

SUMMARY OF THE INVENTION

The present disclosure is directed to inventive oral cleaning devices that deliver user-adjustable coordinated bursts of liquid and air. Various embodiments and implementations herein are directed to oral devices in which a user selects the number of liquid bursts that will be delivered per actuation. The user then activates the selected sequence of bursts with a single actuation. Using the various embodiments and implementations herein, the oral cleaning device can deliver a range of liquid bursts, thereby conserving liquid and preventing repetitive actuation motion by the user.

Generally in one aspect, an oral cleaning device includes a nozzle portion configured to direct a plurality of liquid droplets from a distal end; an actuator; a mode selector; a liquid reservoir wherein in operation liquid is moved from the liquid reservoir into an orifice at the proximal end of the nozzle; a system configured to drive a plunger or piston element toward the proximal end of the nozzle with sufficient force that air acted on by the plunger or piston element is forced into the nozzle at a high rate of speed sufficient to create a burst of liquid droplets when the moving air comes into contact with the liquid; and a control unit configured to control the system to drive the plunger a predetermined number of times in response to a single actuation of the actuator, where the control unit is further configured to accept input from a user via the mode selector, and the mode selector is configured for the user to select a number of liquid bursts that will be delivered in response to a single actuation of the actuator.

According to an embodiment, the oral cleaning device further includes one or more mode indicators configured to indicate the selected number of liquid bursts. The mode indicators can be, for example, lights.

According to an embodiment, the oral cleaning device further includes a power button, where the power button and the mode selector are a single component. Indeed, the mode selector can be further configured to turn the device on or off.

According to an embodiment, the predetermined number of times is at least two times.

According to an embodiment, the oral cleaning device further includes a liquid reservoir door (140) in liquid communication with the liquid reservoir.

According to an embodiment, the control unit is configured to control the system to drive the plunger according to a predetermined pattern in response to a single actuation of the actuator, and wherein the control unit is further configured to accept input from the user via the mode selector to determine the predetermined pattern.

According to an embodiment, the predetermined pattern is at least one burst of liquid followed by at least one jet of liquid.

According to an embodiment, the oral cleaning device further includes a mode indicator for each of a plurality of modes. According to an embodiment, the mode indicator is a series of dots.

Generally, in one aspect, an oral cleaning device includes: a nozzle portion configured to direct a plurality of liquid droplets from a distal end thereof; an actuator; a mode selector; a liquid reservoir where in operation liquid is moved from the liquid reservoir into an orifice at the proximal end of the nozzle; a liquid reservoir door in liquid communication with the liquid reservoir; a system configured to drive a plunger or piston element toward the proximal end of the nozzle with sufficient force that air acted on by the plunger or piston element is forced into the nozzle at a high rate of speed sufficient to create a burst of liquid droplets when the moving air comes into contact with the liquid; a control unit configured to control the system to drive the plunger a predetermined number of times in response to a single actuation of the actuator, where the control unit is further configured to accept input from a user via the mode selector, and the mode selector is configured for the user to select a number of liquid bursts that will be delivered in response to a single actuation of the actuator;

and a plurality of mode indicator lights configured to indicate the selected number of liquid bursts.

It should be appreciated that all combinations of the foregoing concepts and additional concepts discussed in greater detail below (provided such concepts are not mutually inconsistent) are contemplated as being part of the inventive subject matter disclosed herein. In particular, all combinations of claimed subject matter appearing at the end of this disclosure are contemplated as being part of the inventive subject matter disclosed herein.

These and other aspects of the invention will be apparent from and elucidated with reference to the embodiment(s) described hereinafter.

BRIEF DESCRIPTION OF THE DRAWINGS

In the drawings, like reference characters generally refer to the same parts throughout the different views. Also, the drawings are not necessarily to scale, emphasis instead generally being placed upon illustrating the principles of the invention.

DETAILED DESCRIPTION OF EMBODIMENTS

The present disclosure describes various embodiments of an oral cleaning device that delivers coordinated bursts of liquid and air. More generally, Applicants have recognized and appreciated that it would be beneficial to provide an oral cleaning device in which the user selects the number of liquid bursts that will be delivered without requiring manual actuation of each individual liquid burst. For example, the user pre-selects the number of liquid bursts that will be delivered and then activates the delivery of the bursts with a single actuation instead of repetitive actuation. A particular goal of utilization of certain embodiments of the present disclosure is the ability to efficiently clean the oral cavity, particularly the interdental spaces, with liquid dynamics that are selected and easily activated by the user. A wide variety of sensitive areas can be cleaned with the device, including orthodontics, interproximal area, and implants, among others.

Figure 1A:
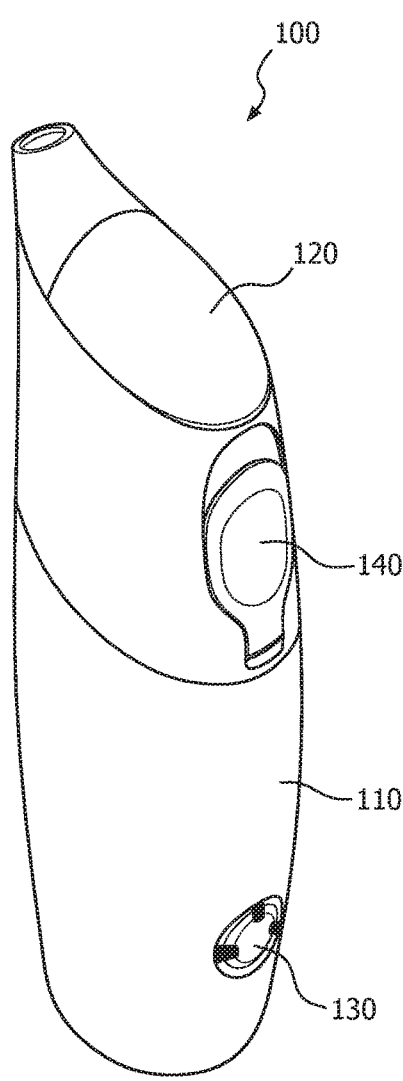
FIG. 1A is a schematic representation of a handle of an oral cleaning device in accordance with an embodiment.
Figure 1B:
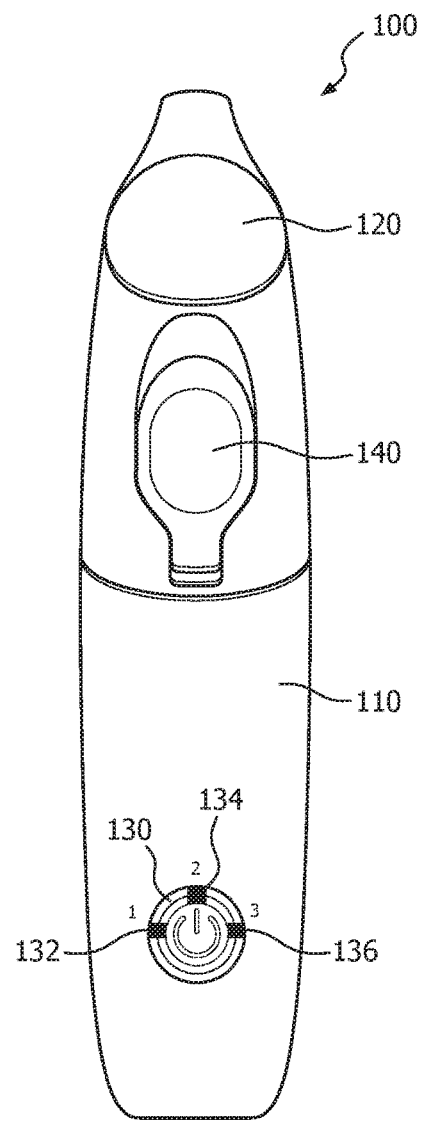
FIG. 1B is a schematic representation of a handle of an oral cleaning device in accordance with an embodiment.

In view of the foregoing, various embodiments and implementations are directed to an oral device in which a user pre-selects the number of coordinated liquid bursts to be delivered from among a predetermined range. Referring to FIG. 1, in one embodiment, is a schematic representation of a handle of an oral cleaning device 100. Oral cleaning device 100 includes an outer housing 110 which can be a plastic or other sufficiently hard or durable plastic. Housing 110 can be ergonomically sized and/or shaped to fit within a variety of hand sizes including children and adults. The handle also includes an actuation button 120 that activates the oral device and causes the delivery of a predetermined sequence of coordinated liquid bursts. During use, actuation button 120 is most comfortably activated by pressing on the button with the first finger, but any finger or the thumb can be used.

Oral cleaning device 100 also includes a power button 130 to activate and inactivate the oral device 100. The button can be disposed on the housing 110 of the device in a location that is generally accessible prior to use as shown in FIG. 1, but does not result in the button inadvertently being touched by the user during use of device 100. To indicate whether the device is on or off, the power button 130 or any other portion of oral cleaning device 100 can include a power indicator such as a light. According to one embodiment, the power indicator also indicates the status of the battery and/or whether the battery is currently charging, among other information.

According to an embodiment, power button 130 also serves as burst number or mode selection button. The user can push the power button 130 to select among a plurality of possible burst numbers. For example, as shown in FIG. 1, the user can push the power button to select either a one-burst mode, a two-burst mode, or a three-burst mode. According to an embodiment, the power button 130 includes indicator lights 132, 134, and 136 to indicate which of the modes is currently selected. For a one-burst mode selection, for example, indicator light 132 may be active. When the two-burst mode is selected, indicator 134 may be active. When the three-burst mode is selected, indicator 136 may be active. Alternatively, selection of the two-burst mode may result in both indicator light 132 and indicator light 134 being activated. Similarly, selection of the three-burst mode can result in all three indicator lights being activated. According to one embodiment, the device may include a single mode selection indicator light that indicates the mode using flashes of light, colors, or a variety of other information-indicating mechanisms. As yet another example, the device may indicate the mode selection using other user indications such as vibration or noise. Although the power button and mode selector/indicator 130 are shown as a single component in FIG. 1, many other variations are possible. For example, the power button and the mode selector/indicator may be separate components placed at separate locations on oral cleaning device 100.

Oral cleaning device 100 can also include a liquid reservoir door 140. The liquid reservoir door opens to a liquid reservoir that receives and stores a liquid used to create the liquid droplets. Liquid reservoir door 140 can be hinged or otherwise attached to the handle in order to allow opening and closing. The door may also be completely removed during refilling of the liquid reservoir.

Figure 2:
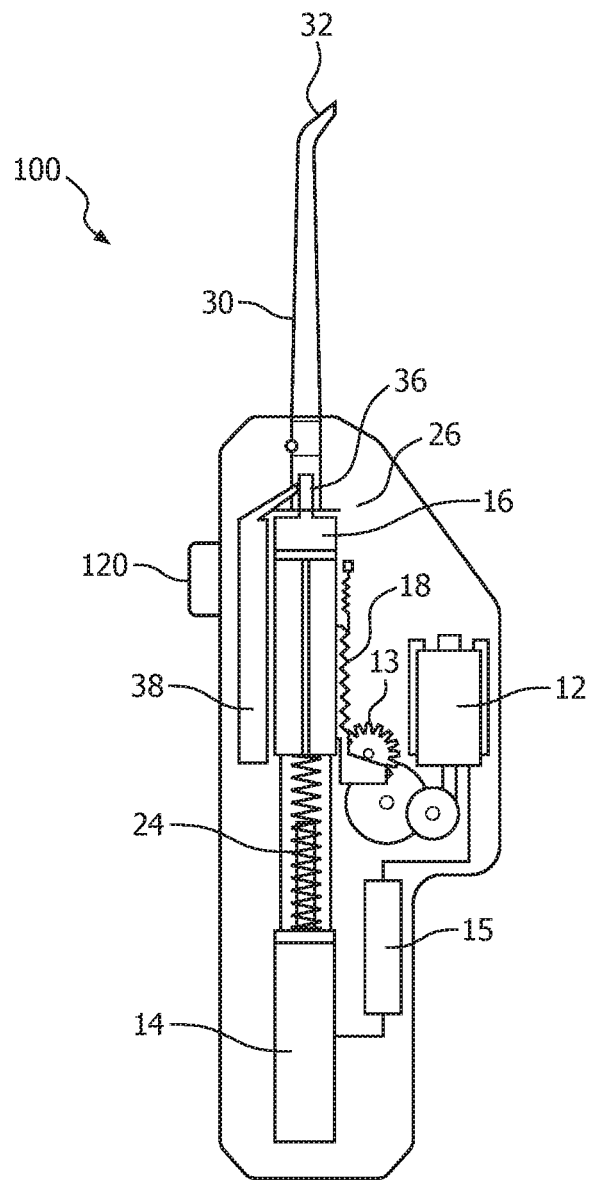
FIG. 2 is a schematic representation of an oral cleaning device in accordance with an embodiment.

Referring to FIG. 2, in one embodiment, is a schematic representation of a drive design for oral cleaning device 100. According to this embodiment, device 100 uses a mechanical spring-drive system to create the selected liquid droplet spray mode for dental cleaning. Device 100 includes a motor and gear train arrangement 12 with a drive gear 13, in which the motor is powered by a battery 14. A control unit 15 is included between the battery and the motor for control of the operation of the appliance. For example, control unit 15 can be activated or controlled by power button 130 (shown in FIG. 1). A button or similar element 120 is used to actuate the device. The gear train drives a plunger/piston member 16 with drive gear 13 engaging a gear rack 18 on plunger/piston 16. As the drive gear 13 rotates, plunger/piston 16 is moved to the rear of the device 100 against the action of a compression spring 24. At the same time, air is drawn into a chamber 26 in the appliance, which could be the interior of the appliance, or a separate volume within the interior of the appliance.

According to an embodiment device 100 includes an elongated nozzle 30 which extends outwardly from the device and can have a curved portion 32 at the distal end thereof, through which a spray of liquid droplets is directed for cleaning action against dental regions of the teeth. The curved portion 32 assists in convenient positioning of the nozzle 30 in the mouth by the user. At the proximal end of the nozzle is an orifice 36. Orifice 36 can vary in size, typically between 0.5 mm and 10 mm. As indicated above, when the plunger/piston 16 is moved to the rear by the action of the motor and gear train 12, air is drawn into chamber 26, either through orifice 36 or alternatively, through a one-way check valve in the body of the appliance, which communicates with chamber 26.

Device 100 also includes an internal liquid reservoir 38 for water, mouthwash, cleaning liquid, or other liquid. The liquid reservoir 38 is in communication with liquid reservoir door 140, shown in FIG. 1, through which liquid can be added to the reservoir. Liquid in the reservoir is moved to the vicinity of the orifice 36 within the nozzle, typically by a pump, by passive aspiration, or by another mechanism.

Drive gear 13 in the embodiment shown has an open space (teeth missing) at a selected position on its periphery, such that when the open space comes adjacent the gear rack 18 on the plunger/piston, the plunger releases, since there are no meshed gears to hold it back, at high speed toward orifice 36 by the action of compression spring 24 moving toward its rest (non-compressed) position. This action is sufficient to drive the air in chamber 26 at high speed through orifice 36. When the fast-moving air comes into contact with the liquid which is adjacent orifice 36, a spray of liquid droplets is produced.

The liquid droplets can be of various sizes, and the speed of the droplets can vary from relatively low speed, e.g. 10 meters per second, to a high speed of 200 meters per second or even greater. Typically, however, a 50 m/sec droplet velocity with droplets in a size range of 5 microns-0.5 mm will provide effective dental cleaning.

Control unit 15 controls the above-described operation depending on the mode setting and in response to each actuation. If the mode setting is for more than a single burst, control unit 15 quickly cycles the drive gear 13 to deliver the number of bursts selected. Control unit 15 may include computer hardware and/or software with button and sensor inputs, and outputs in electrical control of motors, pumps, and optionally valves to deliver the user-selected number of liquid-air bursts.

Figure 3:
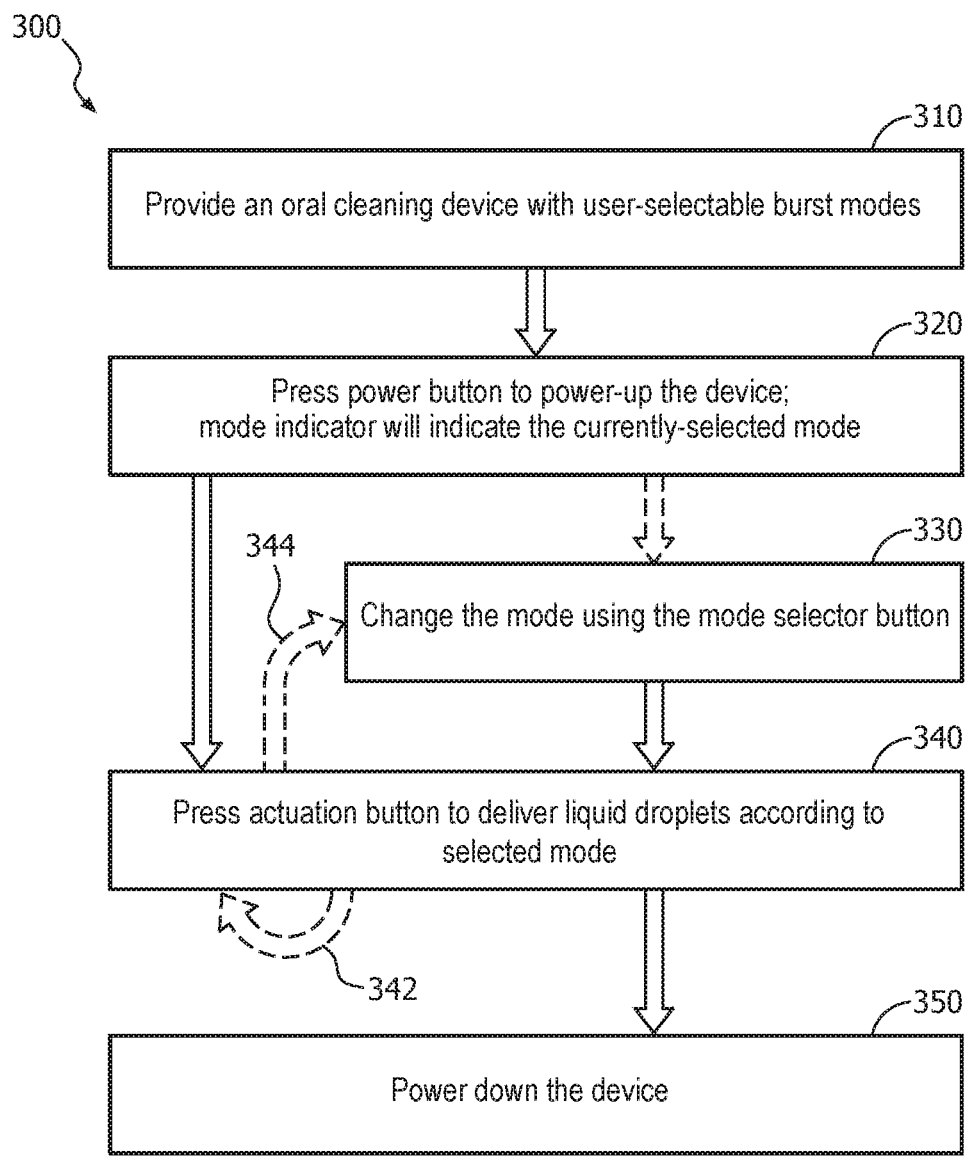
FIG. 3 is a flowchart of a method for cleaning teeth with an oral cleaning device in accordance with an embodiment.

Referring to FIG. 3, in one embodiment, is a flowchart of a method 300 for oral cleaning using oral cleaning device 100. In step 310, a cleaning device 100 with user-selectable burst modes is provided. The cleaning device 100 can be any of the devices described or otherwise envisioned herein. In step 320 of the method, the user activates the device by holding down power button 130 until a power indicator, such as a light, indicates that the device is powered. When the device is activated by pressing button 130, one of indicator lights 132, 134, or 136 will illuminate to show the current mode setting. For example, if a three-burst mode is the current mode setting, then indicator light 136 will be illuminated. A single-burst mode and a two-burst mode are indicated by illumination of indicator light 132 and 134 respectively. Other combinations of indicator lights are contemplated, including the illumination of all three lights 132, 134, 136, for example, in the event of a three-burst mode setting, or two lights, 132 and 134, in the event of two-burst mode setting.

At step 330 of the method the user changes the burst mode using a selection button, which may or may not be the same as power button 130. The user can cycle through the available modes by pressing the button until she arrives at the desired mode. For example, if the mode currently selected—or automatically selected at power-up—is single-burst mode, button 130 is pressed once to change the mode to two-burst mode, and indicator light 134 will illuminate. Pressing button 130 again will change the mode to three-burst mode and indicator light 136 will illuminate. Pressing the burst number selection again will change the mode to one-burst mode and indicator light 132 will illuminate. Alternatively, pressing the burst number selection again can power-down the device.

At step 340 of the method, the user causes delivery of liquid bursts by pressing actuation button 120. Pressing button 120 causes a single burst or a series of bursts of liquid to be delivered at high velocity through the nozzle 30. The particular selected burst sequence generated depends upon the mode setting selected in the previous step. As indicated by arrow 342, the user can repeat step 340 as many times as needed. Additionally, as indicated by arrow 344, the user can return to step 330 to adjust the mode to a different number of bursts.

At step 350 of the method the user inactivates the device, for example, by pressing and holding power button 130 for a period of time, such as one second or longer. According to an embodiment the device will retain the user-selected mode setting in memory such that the same mode will be initiated when the device is next turned on. According to one embodiment, in order to conserve power the device automatically powers down after a predetermined period of not being used.

Figure 4:
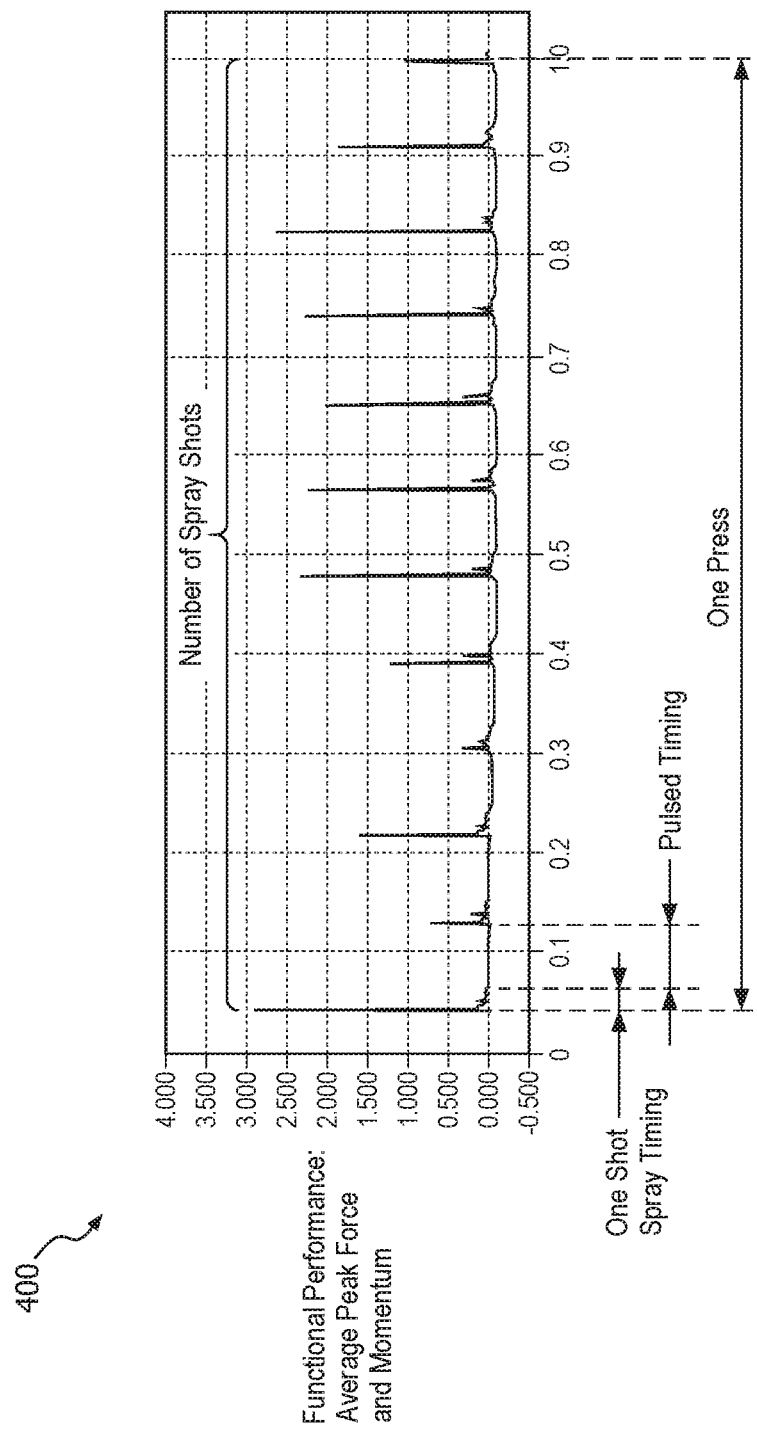
FIG. 4 is a graph of a sequence of liquid bursts delivered by an oral cleaning device in accordance with an embodiment.

Referring to FIG. 4 is a performance graph 400 of oral cleaning device 100 in accordance with an embodiment. It is shown in the graph that device 100 is capable of operating at up to 12 bursts per second. Accordingly, device 100 is capable of generating more than three bursts per button press within a short period of time. For example, although embodiments described herein include one-, two-, and three-burst modes, other modes with additional bursts are possible. According to an embodiment, a typical burst "event" duration initiated by a single press of the actuating button can be about one second or less. Within that second, each burst of a triple burst sequence may last 0.05 seconds or less, spaced by about 0.07 seconds or more in order to allow the mechanism to reset for the next burst. Many other configurations are possible, however, depending upon the device, the user settings, and/or other factors.

Figure 5:
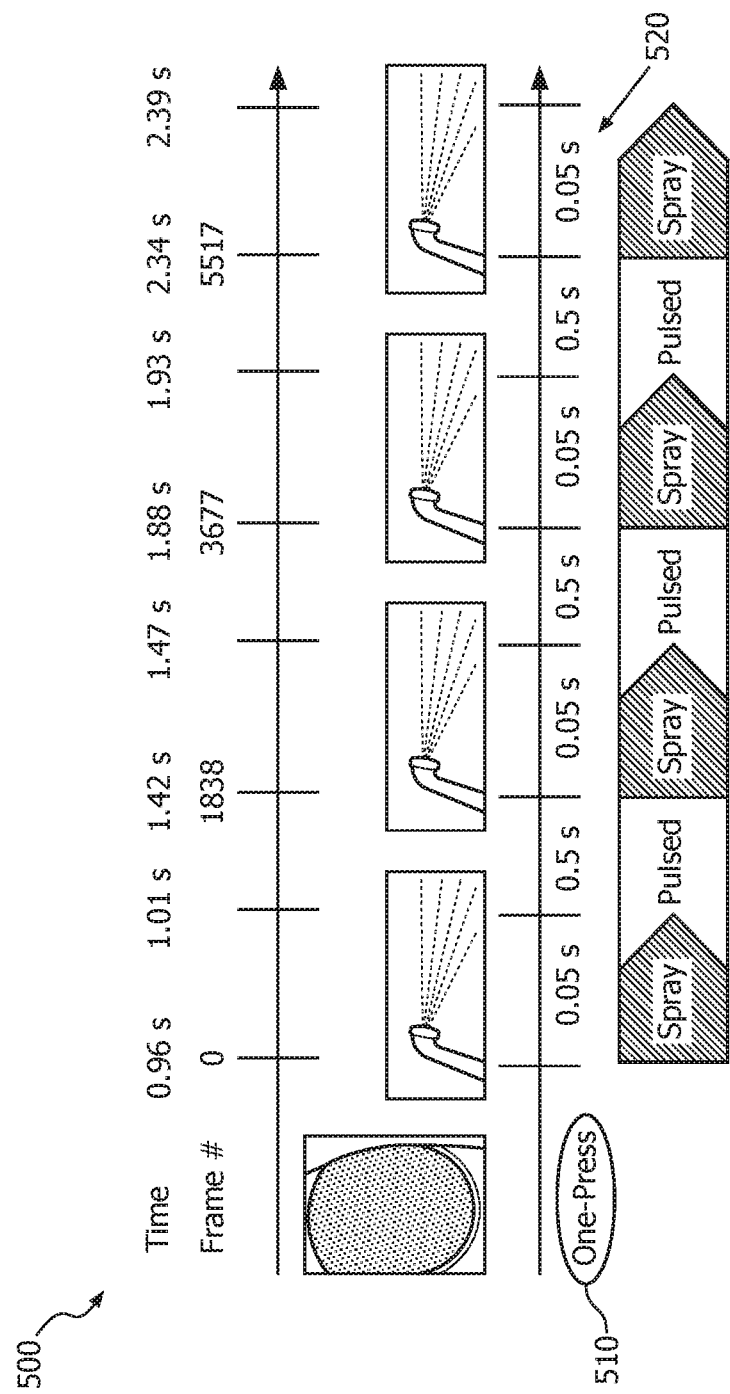
FIG. 5 is a schematic representation of a sequence of liquid bursts delivered after a single actuation of an oral cleaning device in accordance with an embodiment.
Figure 6A:
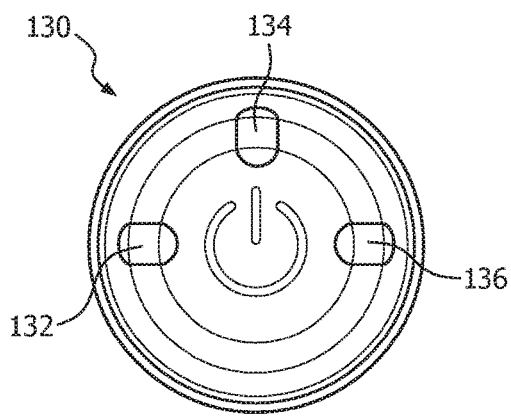
FIG. 6A is a front view of a burst selection button in accordance with an embodiment.
Figure 6B:
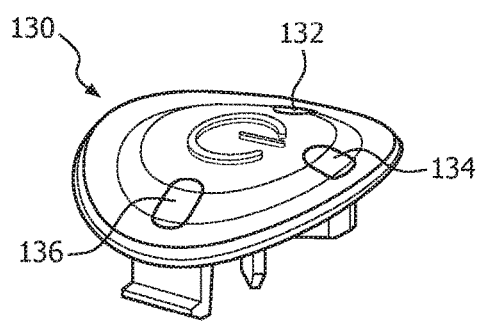
FIG. 6B is a perspective side view of a burst selection button in accordance with an embodiment.
Figure 6C:
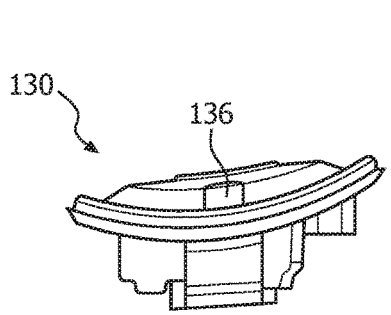
FIG. 6C is a side view of a burst selection button in accordance with an embodiment.
Figure 6D:
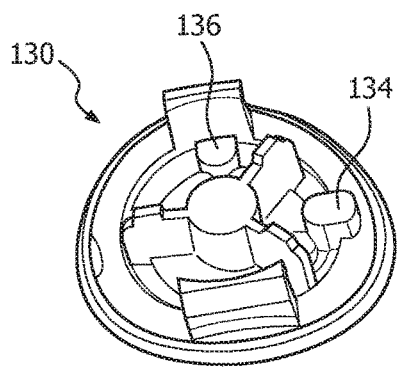
FIG. 6D is a reverse view of a burst selection button in accordance with an embodiment.

Referring to FIG. 5, according to an embodiment, is an example operating mode for device 100. The example operating mode in FIG. 5 is an eight-burst mode of operation 500. In this particular sequence 520, a single press 510 of the actuation button 120 initiates a sequence of spray that is followed by a pulse, repeating the cycle four times. The entire burst duration is shown to be about 1.35 seconds. Other modes of operation, such as two-burst modes or pulses separated by no activity, or three-burst modes or pulses separated by no activity, can be achieved by changing the mode setting.

Referring to FIGS. 6A through 6D is an embodiment of the mode select/power button 130. Mode selection button 130 is configured to conform to the handle of device 100, and therefore is slightly curved. A power indicator is located in the center of the button, and can be a light. In addition, one or more indicator lights may be placed on or adjacent to button 130. According to an embodiment three indicator lights 132, 134, and 136 are disposed around the perimeter of button 530. Each light illuminates as necessary to show the current mode setting. The indicator lights can be any color including yellow, green, or red, and can convey information about the setting, battery, or a variety of other information.

Figure 7:
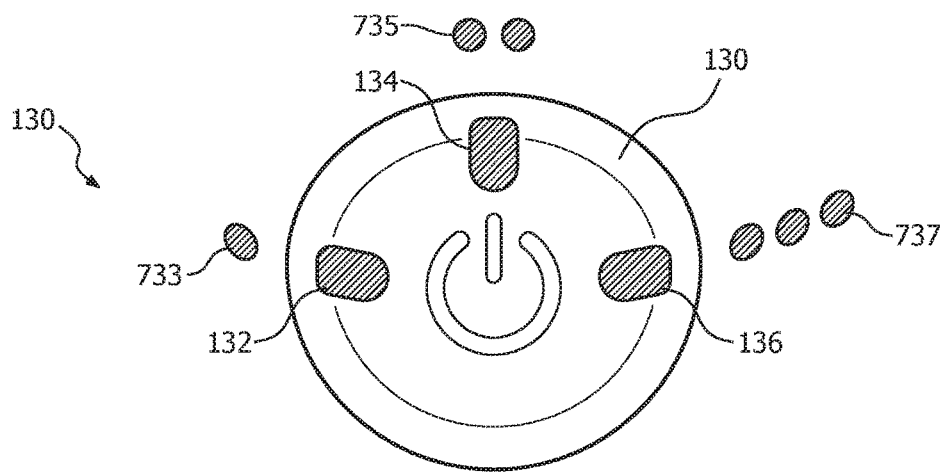
FIG. 7 is a front view of a burst selection button in accordance with an embodiment.

Referring to FIG. 7 is a mode select/power button 130. A power indicator is located in the center of the button, and can be a light or other indicator. In addition, one or more indicator lights are placed on or adjacent to button 130. According to an embodiment three indicator lights 132, 134, and 136 are disposed around the perimeter of button 130. Each light illuminates as necessary to show the current mode setting. The indicator lights can be any color including yellow, green, or red, and can convey information about the setting, batter, or a variety of other information. Further, according to this embodiment, the handle of device 100 includes mode indicators 733, 735, and 737. One-burst mode indicator 733 is denoted by a single dot, two-burst mode indicator 735 is denoted by two dots, and three-burst mode indicator 737 is denoted by three dots. Accordingly, the user will know exactly how many bursts are to be delivered based on the number of dots next to the active light. For example, when the two-burst mode is selected, indicator light 134 will be lit and the user will know that the selection is for two bursts instead of one burst or three bursts.

According to one embodiment, a combination of bursts and jets is one of the possible settings of device 100. It has been shown that liquid jets are efficient at washing away most biofilm when the biofilm is detached. However, to achieve a satisfactory degree of biofilm damage, high speed jets need to be typically used, potentially causing pain during treatment and requiring relatively large volumes of liquid. Compared to jets, bursts may damage a larger area of biofilm employing a much lower volume of liquid and should provide a more pleasant sensation. However, the damaged biofilm may be washed away less efficiently, limiting the overall degree of biofilm removal.

Therefore, according to an embodiment, device 100 delivers a combination of bursts and jets to more efficiently detach and wash away debris and biofilm from the teeth and oral surfaces. According to one embodiment, an initial burst or number of bursts will damage a large area of the biofilm and a subsequent jet will flush the damaged biofilm away, making use of its larger liquid volume (which can be approximately five times the volume of the burst). The order, burst then jet, is important since the washing-away effect of the jet needs to be subsequent to the damaging action of the burst. According to another embodiment, one or more initial jets are used to damage the biofilm followed by a burst or number of bursts to further damage the biofilm and/or to wash the damaged biofilm away.

Figure 8:
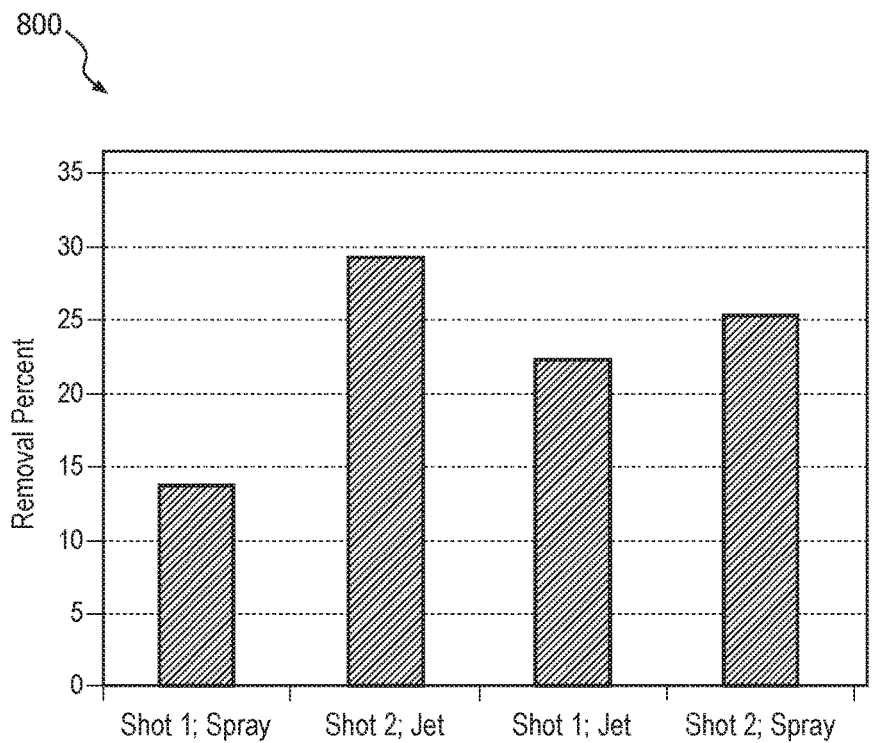
FIG. 8 is a graph of the percent of a sample surface cleaned by different fluidic treatments in accordance with an embodiment.

Referring to FIG. 8, in one embodiment, is a graph 800 of the percent of biofilm removal from a test surface using a combination of bursts and/or jets. As shown in FIG. 8, the biofilm on the test surface was first treated with a burst ("spray") having a droplet diameter with wide distribution of ~100 μm, typical speed of 30-100 m/s, and volume of ~25 μL. This resulted in removal of approximately 13-14% of the biofilm. However, following the initial burst with a jet (speed: ~50 m/s; volume: ~100 μL) increased the removal of biofilm significantly to almost 30%. In other tests the order was inverted and the biofilm was treated first with a jet (the third bar) and then with a burst (the fourth bar). This method only removed approximately 25% of the biofilm. The first order—burst then jet—proved to be significantly more effective.

Device 100 can be configured to provide any combination of burst and jet. For example, the feeding pump can be configured such that a low volume of liquid is ejected first as a burst. Then the feeding pump would eject a larger volume of liquid as a jet. Alternatively, the volume could be kept constant but the ejection mechanism could be configured to deliver the burst and jet differently, such as changing the strength of the force driving the piston. This force would be larger when a burst is created and lower for the subsequent jet. Alternatively, the geometry of the nozzle and/or of the pressure chamber may be configured to produce the desired effect. For example, the feeding nozzle could be increased for the burst and then decreased for the subsequent jet. According to yet another embodiment, the closing value could be configured to be less stiff for the burst and stiffer for the jet. Further, the characteristics of the liquid can be modified or different between the burst and the jet, for instance using a larger density fluid in the second.

All definitions, as defined and used herein, should be understood to control over dictionary definitions, definitions in documents incorporated by reference, and/or ordinary meanings of the defined terms.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of."

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified.

It should also be understood that, unless clearly indicated to the contrary, in any methods claimed herein that include more than one step or act, the order of the steps or acts of the method is not necessarily limited to the order in which the steps or acts of the method are recited.

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

While several inventive embodiments have been described and illustrated herein, those of ordinary skill in the art will readily envision a variety of other means and/or structures for performing the function and/or obtaining the results and/or one or more of the advantages described herein, and each of such variations and/or modifications is deemed to be within the scope of the inventive embodiments described herein. More generally, those skilled in the art will readily appreciate that all parameters, dimensions, materials, and configurations described herein are meant to be exemplary and that the actual parameters, dimensions, materials, and/or configurations will depend upon the specific application or applications for which the inventive teachings is/are used. Those skilled in the art will recognize, or be able to ascertain using no more than routine experimentation, many equivalents to the specific inventive embodiments described herein. It is, therefore, to be understood that the foregoing embodiments are presented by way of example only and that, within the scope of the appended claims and equivalents thereto, inventive embodiments may be practiced otherwise than as specifically described and claimed. Inventive embodiments of the present disclosure are directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the inventive scope of the present disclosure.

What is claimed is:

1. A handheld oral cleaning device comprising:
    a nozzle portion having a proximal end and distal end, wherein the nozzle portion is configured to direct a burst of liquid droplets from the distal end thereof; and
    a handle portion comprising:
        an actuator;
        a burst mode selector;
        a liquid reservoir wherein in operation a liquid is moved from the liquid reservoir into an orifice at a proximal end of the nozzle portion;
        a system driving a plunger or piston element toward the proximal end of the nozzle portion with sufficient force that air acted on by the plunger or piston element is forced into the nozzle portion at a high rate of speed sufficient to create a burst of liquid droplets when the moving air comes into contact with the liquid; and
        a control unit configured to control the system to drive the plunger or piston element a predetermined fixed number of times in response to a single actuation of the actuator to create said predetermined fixed number of liquid bursts;
        the control unit further configured to accept input from a user via the burst mode selector, wherein the control unit is configured to provide each of a one-burst mode, a two-burst mode, and a three-burst mode corresponding to the predetermined fixed number of liquid bursts, and wherein the burst mode selector is configured for the user to select a number of consecutive liquid bursts that will be delivered in response to a single actuation of the actuator; and
        a plurality of burst mode indicator lights configured to indicate the selected number of consecutive liquid bursts.

2. The oral cleaning device of claim 1, further comprising a power button, wherein the power button and the burst mode selector are a single component.

3. The oral cleaning device of claim 1, wherein the burst mode selector is further configured to turn the device on or off.

4. The oral cleaning device of claim 1, further comprising a liquid reservoir door in liquid communication with the liquid reservoir.

5. The oral cleaning device of claim 1, wherein the liquid is water.

6. The oral cleaning device of claim 1, wherein the liquid is mouthwash.

7. The oral cleaning device of claim 1, wherein the control unit is configured to control the system to drive the plunger or piston element according to a predetermined pattern in response to a single actuation of the actuator, and wherein the control unit is further configured to accept input from the user via the burst mode selector to determine the predetermined pattern.

8. The oral cleaning device of claim 7, wherein the predetermined pattern is two consecutive bursts of liquid.

9. The oral cleaning device of claim 1, wherein the plurality of burst mode indicator lights are a series of dots.

10. A handheld oral cleaning device comprising:
    a nozzle portion having a proximal end and distal end, wherein the nozzle portion is configured to direct a burst of liquid droplets from the distal end thereof; and
    a handle portion comprising:
        an actuator;
        a burst mode selector;
        a liquid reservoir wherein in operation a liquid is moved from the liquid reservoir into an orifice at the proximal end of the nozzle portion;
        a liquid reservoir door in liquid communication with the liquid reservoir;
        a system driving a plunger or piston element toward the proximal end of the nozzle with sufficient force that air acted on by the plunger or piston element is forced into the nozzle at a high rate of speed sufficient to create a burst of liquid droplets when the moving air comes into contact with the liquid;
        a control unit configured to control the system to drive the plunger or piston element a predetermined fixed number of times in response to a single actuation of the actuator to create said predetermined fixed number of liquid bursts, wherein the control unit is further configured to accept input from a user via the burst mode selector, wherein the control unit is configured to provide each of a one-burst mode, a two-burst mode, and a three-burst mode corresponding to the predetermined fixed number of liquid bursts, wherein the burst mode selector is configured for the user to select a number of consecutive liquid bursts that will be delivered in response to a single actuation of the actuator; and a plurality of burst mode indicator lights configured to indicate the selected number of consecutive liquid bursts.

* * * * *